(12) United States Patent
Targosz (10) Patent No.: US 9,250,223 B2
(45) Date of Patent: *Feb. 2, 2016

(54) METHOD AND APPARATUS FOR SENSING MAGNETIC RADIATION THROUGH TAGGING

(71) Applicant: Thomas C. Targosz, New Baltimore, MI (US)

(72) Inventor: Thomas C. Targosz, New Baltimore, MI (US)

(*) Notice: Subject to any disclaimer, the term of this patent is extended or adjusted under 35 U.S.C. 154(b) by 568 days.

This patent is subject to a terminal disclaimer.

(21) Appl. No.: 13/667,411

(22) Filed: Nov. 2, 2012

(65) Prior Publication Data

US 2013/0055789 A1 Mar. 7, 2013

Related U.S. Application Data

(60) Continuation-in-part of application No. 13/465,537, filed on May 7, 2012, now abandoned, which is a continuation of application No. 13/033,203, filed on Feb. 23, 2011, now Pat. No. 8,198,887, which is a division of application No. 11/935,605, filed on Nov. 6, 2007, now Pat. No. 7,923,992, which is a continuation-in-part of application No. 10/808,750, filed on Mar. 25, 2004, now Pat. No. 7,148,678, and a continuation-in-part of application No. 11/608,979, filed on Dec. 11, 2006, now Pat. No. 7,327,136.

(60) Provisional application No. 60/864,422, filed on Nov. 6, 2006, provisional application No. 60/864,479, filed on Nov. 6, 2006, provisional application No. 60/870,984, filed on Dec. 20, 2006, provisional application No. 60/946,447, filed on Jun. 27, 2007, provisional application No. 60/975,550, filed on Sep. 27, 2007, provisional application No. 61/555,614, filed on Nov. 4, 2011.

(51) Int. Cl.

| | | |
|---|---|---|
| G01N 27/74 | (2006.01) | |
| G01N 27/82 | (2006.01) | |
| G01N 33/42 | (2006.01) | |
| G01R 33/12 | (2006.01) | |
| G05D 11/13 | (2006.01) | |
| G01N 33/44 | (2006.01) | |

(52) U.S. Cl.
CPC ............. *G01N 33/42* (2013.01); *G01R 33/12* (2013.01); *G05D 11/135* (2013.01); *G01N 27/74* (2013.01); *G01N 27/82* (2013.01); *G01N 33/44* (2013.01)

(58) Field of Classification Search
CPC ...... G01N 27/82; G01N 27/902; G01N 27/74
USPC ................................................. 324/240, 204
See application file for complete search history.

(56) References Cited

U.S. PATENT DOCUMENTS

| | | |
|---|---|---|
| 4,686,469 A | 8/1987 | Lewis |
| 4,816,758 A | 3/1989 | Theissen et al. |

(Continued)

*Primary Examiner* — Reena Aurora
(74) *Attorney, Agent, or Firm* — Fraser Clemens Martin & Miller LLC; William J. Clemens (57) ABSTRACT

A method and an apparatus for monitoring a material includes adding tagging particles to the material, sensing the tagging particles in the material for an even distribution throughout the material, forming a part from the material if the tagging particles are evenly distributed throughout the material, sensing the tagging particles in the part to determine a physical characteristic of the part, placing the part in operation if the determined physical characteristic is within a predetermined specification, sensing the tagging particles in the part during operation to detect at least one of wear and damage to the part, and generating an indication to a user upon detection of the at least one of wear or damage to the part.

7 Claims, 4 Drawing Sheets

(56) References Cited

U.S. PATENT DOCUMENTS

| | | |
|---|---|---|
| 5,315,243 A | 5/1994 | Kempster et al. |
| 5,831,151 A | 11/1998 | Ondrus et al. |
| 6,560,544 B1 | 5/2003 | Ondrus |
| 7,148,678 B1 | 12/2006 | Targosz |
| 7,327,136 B2 | 2/2008 | Targosz |
| 7,923,992 B2 | 4/2011 | Targosz |
| 8,054,065 B2 * | 11/2011 | Targosz ............... 324/204 |
| 8,198,887 B2 | 6/2012 | Targosz |
| 8,269,483 B2 * | 9/2012 | Targosz ............... 324/204 |

* cited by examiner

FIG. 8 ent flowing adjacent said second sensor; a control means responsive to said first and second sense signals for calculating a ratio of the volumes of the first and second components in the mixture, and wherein at least one of said first and second sensors has a generally tubular body with a central passage through which material flows, an inner sense coil extending about a circumference of said passage, a drive coil extending about a circumference of said inner sense coil, and an outer sense coil extending about a circumference of said drive coil; and a master for calibrating said first and second sensors, said first and second sensors each having a passage through which material flows, said master having a body with a smaller diameter end sized to fit into said passages and a larger diameter end sized for use as a handle, said body further having a core formed from a filler material and a predetermined percentage of the ferrous taggant particles.

METHOD AND APPARATUS FOR SENSING MAGNETIC RADIATION THROUGH TAGGING

CROSS-REFERENCE TO RELATED APPLICATION

This application is a continuation-in-part of the co-pending U.S. patent application Ser. No. 13/465,537 filed May 7, 2012, which is a continuation of U.S. patent application Ser. No. 13/033,203, filed Feb. 23, 2011, now U.S. Pat. No. 8,198,887, which is divisional of U.S. patent application Ser. No. 11/935,605, filed on Nov. 6, 2007, now U.S. Pat. No. 7,923,992, which is a continuation-in-part of U.S. patent application Ser. No. 10/808,750, filed on Mar. 25, 2004, now U.S. Pat. No. 7,148,678, and U.S. patent application Ser. No. 11/608,979 filed on Dec. 11, 2006, now U.S. Pat. No. 7,327,136, and claims the benefit of U.S. provisional patent application Ser. Nos. 60/864,422 filed Nov. 6, 2006; 60/864,479 filed Nov. 6, 2006; 60/870,984 filed Dec. 20, 2006; 60/946,447 filed Jun. 27, 2007; and 60/975,550 filed Sep. 27, 2007.

This application claims the benefit of U.S. provisional patent application Ser. No. 61/555,614 filed Nov. 4, 2011.

FIELD OF THE INVENTION

This invention relates to sensing magnetic radiation in tagged materials for detecting problems in materials such as rubber, plastics, liquids, non-magnetic materials etc. More particularly, the invention is directed to testing any material where tagging particles can be added or evenly distributed and then the tagged material tested for problems such as deterioration, cracks, etc.

BACKGROUND OF THE INVENTION

Two-part adhesives, mixed at the time of use, are well known and are used throughout many industries to bond components together. Such adhesives exhibit a faster dry time, longer shelf life, and stronger adhesive characteristics than typical one part adhesives. One requirement of two-part adhesives is to keep the mixture of the parts at the correct ratio to obtain a reaction that will correctly form the adhesive. It often is difficult to monitor the mixing ratio in a production setting where the adhesive parts are being mixed and dispensed as needed on a manufacturing line.

A system and a method for monitoring the proportional volume of constituents provided to an adhesive mixture are shown in the U.S. Pat. No. 5,831,151. Ferromagnetic tagging material particles are suspended in one of the two constituent parts used in the mixture. A first tagging material sensor is utilized to monitor the flow of the tagged part to the mixing area and a second tagging material sensor is utilized to monitor the mixed parts as they flow to a dispenser nozzle. A monitor calculates the volumetric ratio of the two constituents based upon the concentration of the tagging material and a warning is given when the calculated ratio exceeds predetermined limits. Although the preferred embodiment of the present invention is discussed in terms of a two component mixture, this system can be used with more than two component mixtures.

U.S. Pat. No. 7,148,678 describes a ferrous magnetic taggant system for monitoring a ratio of at least two components being combined in a mixture, comprising: a first sensor for generating a first sense signal representing an amount of ferrous taggant particles per unit volume of a first component flowing adjacent said first sensor; a second sensor for generating a second sense signal representing an amount of ferrous taggant particles per unit volume of a mixture of the first component and a ferrous taggant particle free second component flowing adjacent said second sensor; a control means responsive to said first and second sense signals for calculating a ratio of the volumes of the first and second components in the mixture, and wherein at least one of said first and second sensors has a generally tubular body with a central passage through which material flows, an inner sense coil extending about a circumference of the passage, a drive coil extending about a circumference of the inner sense coil, and an outer sense coil extending about a circumference of the drive coil; c) providing control means for calculating a ratio of the volumes of the first and second components in the mixture; d) generating a sine wave test signal with a frequency of "n" times a frequency of the first and second sense signals; e) gathering four points ninety degrees apart for each of "n" cycles of the test signal; f) subtracting a first one of the points from a third one of the points and subtracting a second one of the points from a fourth one of the points to obtain a pair of points for each of the cycles; and g) averaging a first one of all of the pairs of points and averaging a second one of all of the pairs of points to obtain first and second averages respectively, the first and second averages representing an amplitude and phase of the first and second sense signals.

U.S. Pat. No. 7,148,678 further describes a ferrous magnetic taggant system for monitoring a ratio of at least two components being combined in a mixture, comprising: a first sensor for generating a first sense signal representing an amount of ferrous taggant particles per unit volume of a first component flowing adjacent said first sensor; a second sensor for generating a second sense signal representing an amount of ferrous taggant particles per unit volume of a mixture of the first component and a ferrous taggant particle free second component flowing adjacent said second sensor; and a control means responsive to said first and second sense signals for calculating a ratio of the volumes of the first and second components in the mixture, wherein said control means includes a filter that generates a sine wave test signal with a frequency of "n" times a frequency of said first and second sense signals, said filter gathering four points ninety degrees apart for each of "n" cycles of the test signal, said filter subtracting a first one of the points from a third one of the points and subtracting a second one of the points from a fourth one of the points to obtain a pair of points for each of the cycles, and said filter averaging a first one of all of said pairs of points and averaging a second one of all of said pairs of points to obtain first and second averages respectively, said first and second averages representing an amplitude and phase of said first and second sense signals.

In addition, U.S. Pat. No. 7,148,678 describes a method of monitoring a volume ratio of at least two components mixed together comprising the steps of: a) providing a first sensor for generating a first sense signal representing an amount of ferrous taggant particles per unit volume of a first component flowing into a mixing device; b) providing a second sensor generating a second sense signal representing an amount of ferrous taggant particles per unit volume of a mixture of the first component and a ferrous taggant particle free second component flowing in the mixing device, and wherein at least one of the first and second sensors has a generally tubular body with a central passage through which material flows, an inner sense coil extending about a circumference of the passage, a drive coil extending about a circumference of the inner sense coil, and an outer sense coil extending about a circumference of the drive coil; c) providing control means for calculating a ratio of the volumes of the first and second components in the mixture; d) providing a master for calibrating the first and second sensors, the first and second sensors each having a passage through which material flows, the master having a body with a smaller diameter end sized to fit into the passages and a larger diameter end sized for use as a handle, the body further having a core formed from a filler material and a predetermined percentage of the ferrous taggant particles; and e) inserting the smaller diameter end into the passage of one of the first and second sensors.

U.S. Pat. No. 7,327,136 describes a method of monitoring a volume ratio of at least two components mixed together comprising the steps of: a. mixing a predetermined amount of ferrous taggant particles with a predetermined first volume of a first component of a building material to prepare a first mixture in a first mixing device; b. providing a first sensor for generating a first sense signal representing an amount of ferrous taggant particles per unit volume of the first mixture flowing into a second mixing device; c. mixing a predetermined second volume of a second component of the building material with the first mixture to prepare a second mixture in the second mixing device; d. providing a second sensor generating a second sense signal representing an amount of ferrous taggant particles per unit volume of the second mixture flowing from the second mixing device; e. providing a control means for calculating a ratio of the volumes of the first and second components in the second mixture in response to said first and second sense signals; and f. generating a sine wave test signal with a frequency of "n" times a frequency of the first and second sense signals, gathering four points ninety degrees apart for each of "n" cycles of the test signal, subtracting a first one of the points from a third one of the points and subtracting a second one of the points from a fourth one of the points to obtain a pair of points for each of the cycles, and averaging a first one of all of the pairs of points and averaging a second one of all of the pairs of points to obtain first and second averages respectively, the first and second averages representing an amplitude and phase of the first and second sense signals.

U.S. Pat. No. 7,327,136 also describes a method of monitoring a volume ratio of at least two components mixed together comprising the steps of: a. mixing a predetermined amount of ferrous taggant particles with a predetermined first volume of a first component of a building material to prepare a first mixture in a first mixing device; b. providing a first sensor for generating a first sense signal representing an amount of ferrous taggant particles per unit volume of the first mixture flowing into a second mixing device; c. mixing a predetermined second volume of a second component of the building material with the first mixture to prepare a second mixture in the second mixing device; d. providing a second sensor generating a second sense signal representing an amount of ferrous taggant particles per unit volume of the second mixture flowing from the second mixing device; e. providing a control means for calculating a ratio of the volumes of the first and second components in the second mixture in response to said first and second sense signals; and f. providing a master for calibrating the first and second sensors, the first and second sensors each having a passage through which material flows, the master having a body with a smaller diameter end sized to fit into the passages and a larger diameter end sized for use as a handle, the body further having a core formed from a filler material and a predetermined percentage of the ferrous taggant particles, and inserting the smaller diameter end into the passage of one of the first and second sensors.

U.S. Pat. No. 7,327,136 further describes a method of monitoring a volume ratio of at least two components mixed together comprising the steps of: a. mixing a predetermined amount of ferrous taggant particles with a predetermined first volume of a first color component of a coating material to prepare a first mixture in a first mixing device; b. providing a first sensor for generating a first sense signal representing an amount of ferrous taggant particles per unit volume of the first mixture flowing into a second mixing device; c. mixing a predetermined second volume of a second color component of the coating material with the first mixture to prepare a second mixture in the second mixing device; d. providing a second sensor generating a second sense signal representing an amount of ferrous taggant particles per unit volume of the second mixture flowing from the second mixing device; and e. providing a control means for calculating a ratio of the volumes of the first and second components in the second mixture in response to said first and second sense signals to determine a color of the second mixture; and g. generating a sine wave test signal with a frequency of "n" times a frequency of the first and second sense signals, gathering four points ninety degrees apart for each of "n" cycles of the test signal, subtracting a first one of the points from a third one of the points and subtracting a second one of the points from a fourth one of the points to obtain a pair of points for each of the cycles, and averaging a first one of all of the pairs of points and averaging a second one of all of the pairs of points to obtain first and second averages respectively, the first and second averages representing an amplitude and phase of the first and second sense signals.

In addition, U.S. Pat. No. 7,327,136 describes a method of monitoring a volume ratio of at least two components mixed together comprising the steps of: a. mixing a predetermined amount of ferrous taggant particles with a predetermined first volume of a first color component of a coating material to prepare a first mixture in a first mixing device; b. providing a first sensor for generating a first sense signal representing an amount of ferrous taggant particles per unit volume of the first mixture flowing into a second mixing device; c. mixing a predetermined second volume of a second color component of the coating material with the first mixture to prepare a second mixture in the second mixing device; d. providing a second sensor generating a second sense signal representing an amount of ferrous taggant particles per unit volume of the second mixture flowing from the second mixing device; e. providing a control means for calculating a ratio of the volumes of the first and second components in the second mixture in response to said first and second sense signals to determine a color of the second mixture; and f. providing a master for calibrating the first and second sensors, the first and second sensors each having a passage through which material flows, the master having a body with a smaller diameter end sized to fit into the passages and a larger diameter end sized for use as a handle, the body further having a core formed from a filler material and a predetermined percentage of the ferrous taggant particles, and inserting the smaller diameter end into the passage of one of the first and second sensors.

U.S. Pat. No. 7,923,992 describes a method of testing asphalt specimens comprising the steps of: a. manufacturing a test specimen in a laboratory; b. providing a sensor for measuring a field specimen; c. measuring the field specimen with the sensor; d. comparing results of the measuring of the field specimen to the test specimen; and e. determining a mix ratio of the field specimen, wherein said manufacturing of the test specimen comprises the steps of: f. providing a container; g. placing a predetermined quantity of marbles in the container; h. placing a predetermined quantity of tagged material in the container; i. mixing the marbles, gelatin and the tagged material in the container; and j. sensing the tagged material to determine an accuracy of mix ratios of the test specimen, wherein the testing is non-destructive to the tested material.

U.S. Pat. No. 7,923,992 also describes a method of testing asphalt specimens comprising the steps of: providing a container; placing a predetermined first quantity of marbles in the container, each of the marbles having a predetermined diameter; placing a predetermined second quantity of gelatin in the container; placing a predetermined third quantity of tagged material in the container; mixing the marbles, the gelatin and the tagged material in the container to form a test specimen with a known mix ratio; providing a sensor for sensing the tagged material; sensing the tagged material in the test specimen with the sensor to determine a sensed first amount of the tagged material; providing a field specimen including a fourth quantity of the tagged material; sensing the tagged material in the field specimen with the sensor to determine a sensed second amount of the tagged material; comparing the sensed first amount of the tagged material with the sensed second amount of the tagged material to determine a mix ratio of the field specimen.

U.S. Pat. No. 7,923,992 further describes a method of testing asphalt specimens comprising the steps of: providing a container; placing a predetermined first quantity of marbles in the container, each of the marbles having a predetermined diameter; placing a predetermined second quantity of gelatin in the container; placing a predetermined third quantity of tagged material in the container; mixing the marbles, the gelatin and the tagged material in the container to form a test specimen with a known mix ratio; providing an above surface sensor for sensing the tagged material; sensing the tagged material in the test specimen with the sensor to determine a sensed first amount of the tagged material; providing a field specimen including a fourth quantity of the tagged material; sensing the tagged material in the field specimen with the sensor to determine a sensed second amount of the tagged material; comparing the sensed first amount of the tagged material with the sensed second amount of the tagged material to determine a mix ratio of the field specimen.

U.S. Pat. No. 8,198,887 describes a method for inspecting an installed mixed material comprising the steps of: a. positioning a sensor adjacent to or on a finished surface of an installed mixed material containing at least a first material mixed with taggant particles; b. generating a sense signal from the sensor representing an amount of the taggant particles per unit volume of the mixed material below the surface of the mixed material; and c. displaying an indication of a profile of the taggant particles in the mixed material based upon the sense signal.

U.S. Pat. No. 8,198,887 also describes a method for monitoring a mixture ratio of an asphalt paving material prepared for installation comprising the steps of a. positioning a sensor adjacent a surface of an installed asphalt paving material containing a first material with taggant particles and a second material without the taggant particles; b. generating a sense signal from the sensor representing an amount of the taggant particles per unit volume of the asphalt paving material below the surface of the asphalt paving material; and c. displaying an indication of a mixture ratio of the first and second materials based upon the sense signal.

U.S. Pat. No. 8,198,887 further describes an apparatus for inspecting a manufactured mixed material including a plurality of taggant particles comprising: a sensor adapted to be positioned on or adjacent to a finished surface of a manufactured mixed material containing at least a first material and a plurality of taggant particles, the sensor generating a sense signal representing an amount of the taggant particles per unit volume of the mixed material below the surface when positioned on or adjacent to the surface; and a control device responsive to the sense signal for indicating a profile of the taggant particles in the mixed material.

SUMMARY OF THE INVENTION

The invention concerns a method for monitoring a material comprising the steps of: adding tagging particles to a material; sensing the tagging particles in the material for an even distribution throughout the material; forming a part from the material if the tagging particles are evenly distributed throughout the material; sensing the tagging particles in the part to determine a physical characteristic of the part; placing the part in operation if the determined physical characteristic is within a predetermined specification; sensing the tagging particles in the part during operation to detect at least one of wear and damage to the part; and generating an indication to a user upon detection of the at least one of wear or damage to the part.

The invention also concerns a method for monitoring a moving material comprising the steps of: adding magnetic field altering tagging particles to a material; demagnetizing the tagging particles prior to moving the material to a first point; magnetizing the tagging particles at the first point; operating a first magnetic flux sensor at the first point to generate a first signal representing a detection of the magnetized tagging particles as the material leaves the first point; moving the material a predetermined distance from the first point to position the magnetized tagging particles at a second point; operating a second magnetic field sensor at the second point to generate a second signal representing a detection of the magnetized tagging particles when the magnetized tagging particles arrive at the second point; calculating a speed at which the material is moving between the first point to the second point based upon the predetermined distance and an elapsed time between the generation of the first signal and the generation of the second signal; and indicating to a user the speed at which the material is moving.

The invention further concerns an apparatus for monitoring a part containing tagging particles distributed throughout comprising: a magnetic field generator positioned adjacent the part and generating a magnetic field; a first sensor positioned adjacent the part at a first point near the generator for generating a reference signal representing sensed flux; a second sensor spaced from the first sensor and positioned at a second point adjacent the part for generating a damage signal representing sensed flux; and an electronics unit connected to the first and second sensors for demodulating the damage signal with the reference signal to detect a change in the damage signal caused by wear or damage to the part.

The invention also concerns an apparatus for monitoring a part containing tagging particles distributed throughout comprising: a magnetic field generator positioned adjacent the part and generating a magnetic field; a sensor positioned adjacent the part for generating an output signal representing sensed flux; and an electronics unit connected to the sensor for demodulating the output signal by generating a square wave from the output signal and utilizing the square wave to detect a change in the output signal caused by wear or damage to the part and notify an operator of the change.

DESCRIPTION OF THE DRAWINGS

The above as well as other advantages of the present invention will become readily apparent to those skilled in the art from the following detailed description of a preferred embodiment when considered in the light of the accompanying drawings in which.

DETAILED DESCRIPTION OF THE INVENTION

The U.S. provisional patent application Ser. No. 61/555,614 filed Nov. 4, 2011 and U.S. patent application Ser. No. 13/465,537 filed May 7, 2012 are incorporated herein by reference.

The following detailed description and appended drawings describe and illustrate various exemplary embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical.

The method and apparatus according to the invention for sensing magnetic radiation in tagged materials provide a solution for detecting problems in materials such as rubber, plastics, liquids, non-magnetic materials, etc. Any material where tagging particles can be added or evenly distributed can then be tested for problems such as deterioration, cracks, etc. The tagging particles are added to the material prior to manufacture of products and initially tested using sensors according to the invention to ensure the tagging component is evenly distributed. The tagged material then enables the sensors to monitor for defects as the products are manufactured notifying the operator when a defective part is manufactured. After each product is manufactured, the sensors can be used to confirm the product is within specifications.

The sensors according to the invention also can be used for preventative maintenance by monitoring the product during operation. For example, serpentine belts and hoses associated with a vehicle engine can be monitored during operation of the vehicle. The sensors monitor for defects such as cracks and deterioration throughout the part; not only on the surface of the part. The tagging particles mixed with the production material (for example, fiber glass, plastic, rubber, etc.) enables parts to be monitored throughout the life of a product.

It should be noted that the method and apparatus according to the invention is not limited to automotive parts. Industrial belts and hoses, and any part manufactured with the tagging particles can benefit from the technology of this invention. Other examples products that can be tested and monitored are road building materials, construction materials, industrial equipment, etc.

Materials such as rubber, plastic, fiber glass, and any non-magnetic material are difficult to evaluate for flaws in the internal structure due to improper manufacturing or damage due to wearing. Once manufactured, it is difficult to monitor changes due to aging of the material or failure such as cracking. Technologies such as ultrasonic inspection are not practical due to difficulties in coupling the sensor to the part under test. Few practical technologies can be used to study defects within the material without destroying the part. The sensors according to the invention detect problem areas within these parts.

Adding tagging particles to a material provides a method for ensuring:

1. Correct mix ratios during manufacture of the material from which the product will be manufactured.
2. 100 percent inspection during the liquid stage of the product to ensure that the product is mixed with the tagging particles evenly distributed. This is accomplished with an encircling sensor that monitors the material as it flows through the sensor. Various other sensors can monitor this mixture if encircling is not an option.
3. During manufacturing parts are examined to ensure they are made within a specification, dimensionally correct, and problem free without cracks, voids, etc.
4. Monitoring for damage or changes during shipping of the part.
5. Monitoring during construction with the tagged material for density, compaction, thickness, etc.
6. Monitoring for preventative maintenance on a finished product.
7. Detection of problems as they occur during operation of a tagged part and notifying an operator of a problem before failure occurs.

The method and apparatus according to the invention can be used for automotive parts such as hoses, serpentine belts, v-belts, etc. by adding tagging particles to rubber material prior to manufacture of the part. For engine v-belts or hoses, etc., the tagging sensors monitor throughout mixing, manufacturing, construction and while the part is in use. By adding sensors to the at the point of installation of the finished product, the part can be continuously monitored for cracks and deterioration notifying the driver of the automobile that the monitored V-belt or hose is going to fail. V-belts move past a stationary sensor. Stationary sensors can be mounted on a hose to continuously monitor for changes in the hose.

Figure 1:
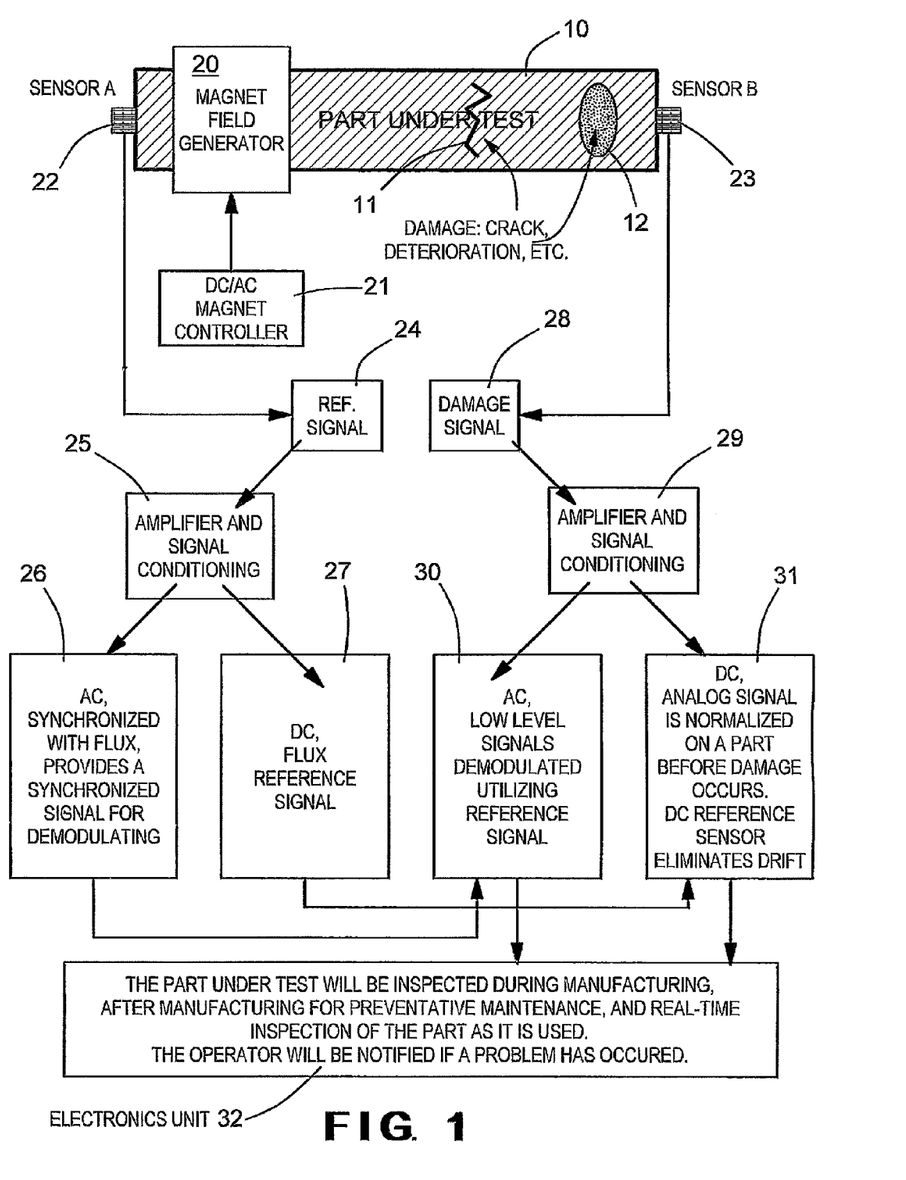
FIG. 1 is a block diagram of system for testing a product according to the invention.

There is shown in FIG. 1 a tagged product under test 10 such as a hose mounted on a vehicle engine (not shown) to be scanned for defects. Typical defects include a crack 11 and an area of deterioration 12. The hose 10 is monitored by observing changes in a magnetic field produced by a magnetic field generator 20 controlled by a DC/AC magnet controller 21. The magnetic field changes are detected by a sensor "A", identified as a first sensor 22, positioned at one end of the hose 10 and a sensor "B", identified as a second sensor 23, positioned at an opposite end of the hose. Any defects between the sensors 22, 23 are monitored. The first sensor 22 generates a reference signal 24 that is input to a first amplifier and signal conditioning circuit 25 that splits the input signal into an AC synchronized with flux component 26 and a DC flux reference signal component 27. The second sensor 23 generates a damage signal 28 that is input to a second amplifier and signal conditioning circuit 29 that splits the input signal into AC low level signals component 30 that is demodulated utilizing the synchronized reference signal 26 and a DC analog signal component 31 that is normalized on the part before damage occurs. The DC reference signal 27 eliminates drift in the DC analog signal 31.

The AC low level signals component 30 and the DC analog signal component 31 are inputs to an electronics unit 32 that processes the signals to generate an indication of a defect or problem to notify a user or operator. The unit 32 also can generate an indication or display of the signal components 30 and 31 and any other signal generated by the apparatus shown in FIG. 1.

The addition of tagging particles to a material can be utilized in various types of applications. When tagging asphalt or cement material, the sensors can monitor mixing, manufacturing, changes caused during transporting, ensure construction is properly done, and indicate that preventative maintenance is required for the finished product. The sensors according to the invention can be used to examine the material in use. For example, the sensors are driven over the finished road for the detection of cracks or changes in the compaction, density and mixture.

The tagging particles can be formed of any material which alters the magnetic field. For example, ferrite particles can be added to a manufacturing material. The magnetic field intensity is proportional to the concentration of ferrite per unit volume of the manufacturing material. If this concentration is altered due to wearing, mixing problems, cracks, etc., the sensors according to the invention can detect the problem. Tagging can be utilized throughout the life of the product.

Another example of a tagging material is aluminum powder. Aluminum powder has a low permeability that will not affect the magnetic field unless an AC magnetic field is applied and eddy currents are detectable. The eddy currents will oppose the applied magnetic field. Eddy current sensors will detect this change in magnetic field.

There is a mathematical relation to the expected affect the tagging will cause the part to exhibit. A sensor encircling the part will linearly display the volume of the material under test. If this volume is disrupted, the sensor will see a change. If the design intentionally changes the volume, a micro-processor is able to calculate the change that should occur. If the calculated and actual results are not within specification, the operator will be notified.

Various sensors are available to perform the method according to the invention based upon factors such as the tagging particle material, the material from which the part is manufactured, the shape of the part and the position and operation of the part in use. Suitable sensors include Hall effect sensors, eddy current sensors, and giant magnetoresistance (GMR) sensors. By applying AC, DC or a combined AC/DC current to various combinations of sensors different characteristics of the parts can be evaluated.

Crack sensors can be driven over the surface of a road or permanently mounted for scanning a V-belt. In the first case, the sensor is moved across the road while in the other situation the sensor is permanently mounted and the belt passes adjacent the sensor. One type of crack sensor according to the invention uses two inductive sensors (various configurations for dual coil sensors include dual-bridge sensors and a separate drive with dual sense windings). The differential crack sensor differentiates the surface and the part material below the surface. Hall sensors or GMR sensors can be wired differentially and similarly to monitor for cracks. Multiple sensors may be required when monitoring a serpentine belt.

The sensors according to the invention can be used to monitor part thickness. At a constant power level from the magnetic field generator a variation in thickness will also affect the sensor signal. This can be used to measure variations in thickness. This assumes that the other conditions remain constant. Alternatively, by varying a power level of the magnetic field the thickness can be determined. As the power level increases the sensor signal varies in a consistent manner until the part is saturated. A different thickness of a part will have a different voltage vs. power relationship when saturated. This can be interpreted using a microprocessor.

The method and apparatus according to the invention can be used to monitor, including but not limited to: thickness; compaction; crack; flow rate; density; mix ratio; and slippage of belts. The sensors used can include: coil sensors; Hall effect sensors; and GMR sensors.

Figure 2:
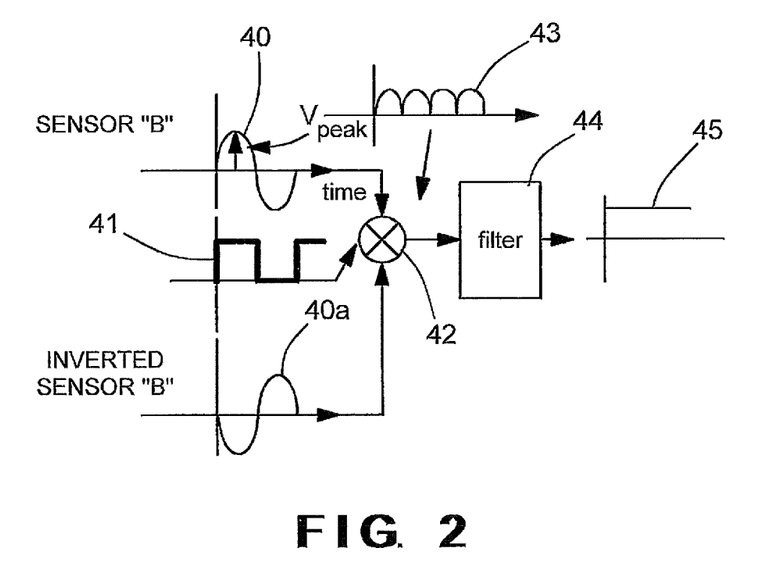
FIG. 2 is a schematic diagram of a portion of the system shown in FIG. 1 with the waveforms of the signals generated.

There is shown in FIG. 2 a schematic diagram of the processing of the signals from the sensors 22 and 23 shown in FIG. 1 showing the waveforms of the signals generated. The "A" sensor 22 is normally located in the near vicinity of the generator 20 at one end of the part as shown in FIG. 1. The sensor 22 monitors the reference flux from the magnetic field generator 20 and generates a representative output signal. The "B" sensor 23 is located at the opposite end of the part and detects changes in the material as very small output signals 40. The "A" sensor output signal will vary according to the flux generated by the magnetic generator 20. The flux is varying in phase with the "B" sensor output signal 40. The large signal output due to the location of the "A" sensor 22 provides a stable reference for demodulation.

The "A" sensor output signal can be converted to a square wave signal 41 that is in phase with the "B" sensor output signal 40. Meanwhile the output signal from the "B" sensor can be amplified. The square wave signal 41 is used to turn on and off analog switches 42 which in turn full wave rectifies the "B" sensor output signal 40 to generate a demodulated signal 43. For example, the switches 42 can pass only the positive portions of the signal 40 and an inverted form of the signal 40 represented by a signal 40a. Mathematically the sine wave of the "B" sensor signal 40 is multiplied by the square wave signal (+−1) 41 of the "A" sensor. The square waves have the fundamental and odd harmonics. Multiplying the square wave and the sine wave results in the sum of the frequencies and the differences. The high frequency sum is easily filtered by a filter 44 from the remaining signal to generate a synchronously demodulated output signal 45. Meanwhile offsets, interfering sine waves of different frequency are easily filtered as long as they are not near the frequency of the generator output. This technique allows recovery of very small damage signals which are often surrounded by electronic noise.

Figure 3:
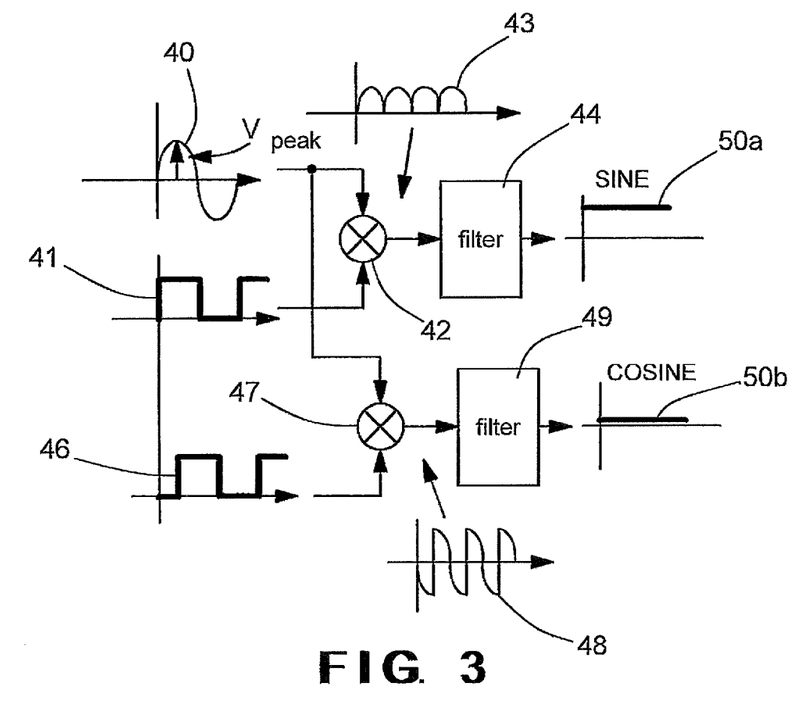
FIG. 3 is a schematic diagram similar to FIG. 2 with a modification to generate phase information.

Alternatively, in applications where phase information is of value, two signals 90° out of phase can be used to generate quadrature square waves 41 and 46 as shown in FIG. 3. The generator will use one of the square waves 41 to produce a magnetic field. Normally the square wave is converted to a sine wave and is used to generate the magnetic field. Multiplying the two square waves 41 and 46 independently by the "B" sensor output signal 40 in the switches 42 and 47 respectively generates the demodulated signals 43 and 48 respectively. Filtering the harmonics from the demodulated signals 43 and 48 with the filters 44 and 49 respectively results in output signals 50a and 50b respectively. The amplitudes of the output signals 50a and 50b correspond to the sine and cosine magnitudes respectively of the resulting wave form. The amplitude will be calculated by taking the square root of the sum of the squares. The angle is determined by taking the inverse tangent of the sine/cos. Direct multiplication of the sine waves can also provide the same results.

Other hardware techniques are alternative solutions including but not limited to peak detection, using a comparator for zero-cross detection of "B" sensor output and then using an "exclusive or" logic gate to separate the phase information, etc. With the high speed microprocessors or signal processors the waveforms can be digitized and mathematically filtered and converted to amplitude and phase. Fast Fourier transform and other sampling techniques are readily available.

The sensor technology according to the invention not only can be used to study the static changes when a part is statically positioned. The technology can be used parts are cycled; for example, a hydraulic hose bending as it is used to open and close a door. The pressure causes changes in the rubber material of the hose. The expansion or contraction of the rubber causes the tagged material to compress-and-decompress. The sensor signals will vary accordingly. If a change occurs in the expected output signals an operator will be notified. This change is analyzed by a microprocessor which then determines if a problem is occurring.

For cost savings the "B" sensor can be eliminated. The "A" sensor 22 generates a larger signal than "B" sensor 23 due to the location of the "A" sensor near the magnetic field generator 20. As damage occurs to the part 10 the signal amplitude will vary. This is a small variation compared to the much larger flux that is present. The damage information can be signal conditioned using the techniques described above. For certain applications this may be sufficient for detecting damage to the part. Bridge configurations of the sensors also can be used.

Figures 4, 5:
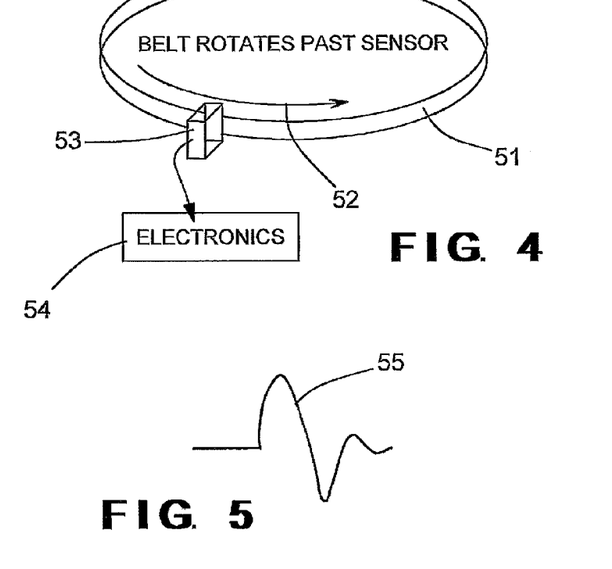
FIG. 4 is a schematic perspective view showing the system according to the invention monitoring a moving belt.
FIG. 5 is a waveform diagram of a signal generated by the system shown in FIG. 4 upon detection of a crack in the belt.

As shown in FIG. 4, a tagged rubber V-belt 51 is being rotated in the direction of an arrow 52. As the belt 51 passes a fixed sensor 53 a crack in the belt will generate a signal from the sensor to an electronics signal processing unit 54. A typical signal 55 generated by the sensor 53 when a crack is detected is shown in FIG. 5. The sensor 53 is mounted near the V-belt 52 in the engine compartment of a vehicle and the electronics unit 54 is mounted in the passenger compartment for notifying the driver before the belt fails.

The sensors according to the invention monitor magnetic fields responding to the tagging particles which are mixed with materials including rubber, fiber glass, cement, asphalt, adhesive, etc. The sensor will detect changes including, density, compaction, cracking, velocity, volume flow, thickness and variation in mixture.

A differential crack sensor can be implemented with two sensors that are positioned next to each other. As the sensors are moved across a surface (or a surface moves past the sensors) the spatial separation causes each sensor to see a pulse similar to a half of a sine wave. This improves the detection of cracks while ignoring low frequency changes such as lift-off variation. One pulse is slightly delayed in time. By subtracting the pulses, the result is a signal similar to the one shown in FIG. 5. The crack sensors can be created using differential sensors made from coils, Hall effect sensors, GMR sensors, and any sensor that measures flux or changes in the flux.

The electronics unit 54 includes analog signal processing, digital signal processing and microprocessor devices that condition signals and determine whether the problem is a crack or some other type of problem. Signal conditioning of the type described above can be used to obtain the defect information. Also subtracting the two sensors and amplifying provides the necessary level for detection of cracks. Sensors are spatially differentiated when the coil passes over a surface.

Additionally the crack sensors are positioned for monitoring the density, compaction, velocity, volume flow, and thickness variation. One of the two sensors used for crack detection can be used for an absolute measurement of these problems or special positioned sensors can be used. The electronics described above is used for these applications. The other one of the two sensors used for crack detection can also separately monitor for detection of changes such as wearing, thickness variation etc. Alternatively, additional sensors can be mounted on a movable arm or on a vehicle which moves over the surface.

Larger belts including serpentine belts can be monitored by using an array of the crack sensors. The microprocessor in the electronics unit 54 aids in multiplexing the array of sensors and evaluating the condition of the belt.

Figure 6:
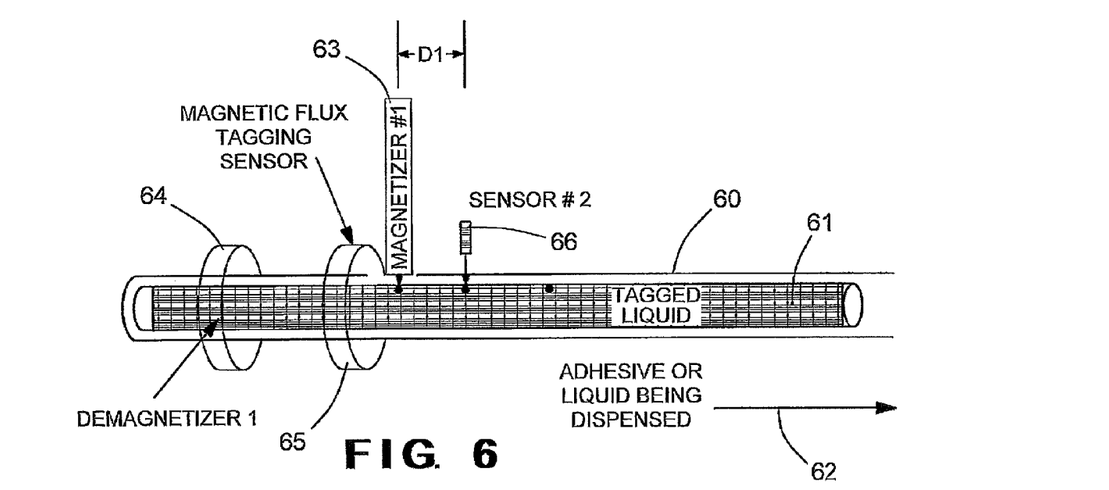
FIG. 6 is a schematic view of the system according to the invention measuring the volume flow of a liquid through a tube.

The method and apparatus according to the invention can be used to measure the flow of liquid and semi-liquid materials. Presently a paddle wheel type of measurement sensor is used which often becomes clogged. Using tagged material, a liquid can be tested for whether the tagged material is correctly mixed and for the rate of the dispensing (flow rate). The amount of liquid material within the sensor can be accurately detected. As shown in FIG. 6, a pipe, hose or tube 60 contains a tagged liquid 61 flowing in the direction of an arrow 62. A magnetizer 63 magnetizes the material at a spot along the tube 60 and the time (t) for the spot to travel a predetermined distance D1 to a position of a sensor can be used to determine the flow speed (speed=D1/t). The flow rate can then be calculated by multiplying the speed by the cross-sectional area of the tube (flow rate=(D1/t)$\times \pi \times r^2$) where "r" is the radius of the tube 60.

The liquid 61 being dispensed has been previously tagged. The liquid 61 in the tube 60 flows through a demagnetizer 64 to ensure that the tagging particles in the liquid are not magnetized. Next, the liquid 61 flows through a first magnetic flux tagging sensor 65 that measures the volume of liquid flowing. If the measured value indicates that the liquid fills 100% of the tube cross section, then the volume will be $D1 \times \pi \times r^2$, where r=radius of the tube 60 transferring the liquid. Then the tagging particles adjacent the magnetizer 63 at a first point are magnetized and flow to a second magnetic flux tagging sensor 66 at a second point where they are detected. The travel time of the liquid 61 from the first point to the second point enables calculation of the volume per second flow rate based upon the distance D1 between the first and second points. This will ensure the correct amount of material is dispensed. The apparatus shown in FIG. 6 also can be used to monitor the speed at which a part is moving. The flow speed and flow rate calculations can be performed by the electronics unit 32 that can indicate the sensed and calculated information to a user.

Figure 7:
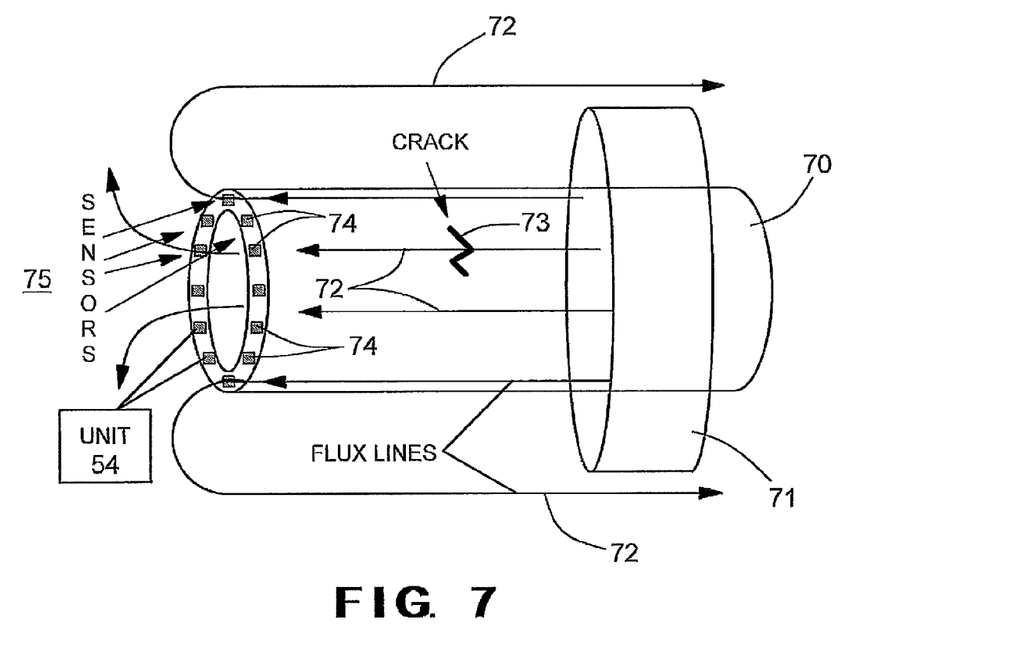
FIG. 7 is a schematic perspective view of a ring array of the sensors for monitoring a hose according to the invention.

A plurality of the sensors according to the invention can be positioned in an array for monitoring a part. FIG. 7 is a schematic perspective view of a ring array 75 of a plurality of sensors 74 for monitoring a hose 70 according to the invention. A magnetic field generator 71 positioned at one end of the hose 70 generates flux lines 72 that are directed parallel to a longitudinal axis of the hose 70 by the tagging particles. The sensors 74 are positioned at an opposite end of the hose 70. Each of the sensors 74 is connected to an electronics unit, such as the electronics unit 54 shown in FIG. 4. Although only two of the sensors 74 are shown connected to the unit 54 for simplification of the drawing, all of the sensors 74 are connected to the unit for multiplexing the signals from the sensors and generating an indication of a defect (such as a crack 73) to a user or operator. The ring array 75 provides a more accurate indication of where the crack 73 is located about a circumference of the hose 70.

Figure 8:
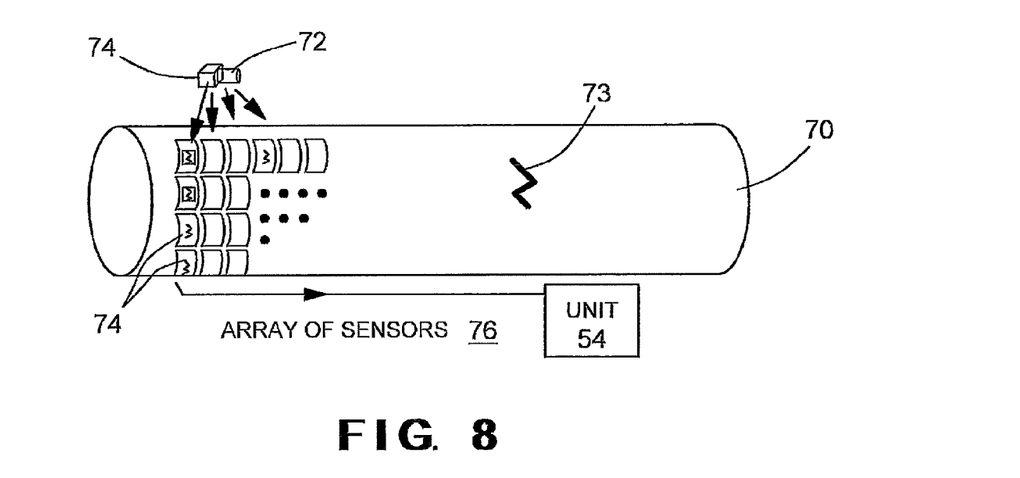
FIG. 8 is a schematic perspective view of a portion of a field array of the sensors for monitoring a hose according to the invention.

FIG. 8 is a schematic perspective view of the hose 70 wherein a plurality of the sensors 74 according to the invention is positioned in a field array 76 for monitoring. The magnetic field generator 70 of FIG. 7 is utilized to generate the flux lines 72 but is not shown. Although only one of the sensors 74 is shown connected to the unit 54 for simplification of the drawing, all of the sensors 74 are connected to the unit for multiplexing the signals from the sensors and generating an indication of a defect to a user or operator. The field array 76 provides a precise indication of where the crack 73 is located on the hose 70 in terms of circumference and distance from the array. In addition, a line of sensors, such as any column of the sensors 74 shown in the FIG. 8, forms a linear array that can be used to monitor a width of a part either as the part moves past the array or as the array moves along the part.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A method for monitoring a material comprising the steps of:
   adding tagging particles to a material;
   sensing the tagging particles in the material for an even distribution throughout the material;
   forming a part from the material if the tagging particles are evenly distributed throughout the material;
   sensing the tagging particles in the part to determine a physical characteristic of the part;
   placing the part in operation if the determined physical characteristic is within a predetermined specification;
   sensing the tagging particles in the part during operation to detect at least one of wear and damage to the part; and
   generating an indication to a user upon detection of the at least one of wear or damage to the part.

2. The method according to claim 1 including sensing the tagging particles in the material during formation of the part and notifying an operator that the part is defective based upon a change in the distribution of the tagging particles.

3. The method according to claim 1 wherein the part is moving during operation and including notifying an operator of the at least one of wear and damage based upon a change in the distribution of the tagging particles.

4. The method according to claim 1 including utilizing crack detection sensors for sensing the tagging particles in the part, the crack detection sensors spatially differentiating to detect surface and below surface cracks and voids in the part.

5. The method according to claim 1 including varying a power of a magnetic field applied to the part and determining a thickness of the part by sensing when the part is saturated with flux.

6. The method according to claim 1 including detecting the at least one of wear and damage with a plurality of sensors positioned in an array exterior to the part.

7. The method according to claim 1 wherein the array is one of a linear array, a ring array and a field array.

\* \* \* \* \*